(12) United States Patent
Richards

(10) Patent No.: US 8,342,004 B2
(45) Date of Patent: *Jan. 1, 2013

(54) GAS ANALYZER

(76) Inventor: Dean John Richards, Midland, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,514

(22) Filed: Apr. 10, 2012

(65) Prior Publication Data

US 2012/0198915 A1 Aug. 9, 2012

Related U.S. Application Data

(63) Continuation of application No. 12/514,951, filed as application No. PCT/US2008/079722 on Oct. 13, 2008, now Pat. No. 8,171,772.

(60) Provisional application No. 60/981,873, filed on Oct. 23, 2007.

(51) Int. Cl.
G01N 1/00 (2006.01)

(52) U.S. Cl. ..................................................... 73/23.41

(58) Field of Classification Search .................. 73/23.2, 73/23.35, 23.41, 23, 2
See application file for complete search history.

(56) References Cited

U.S. PATENT DOCUMENTS

| 2,854,353 | A | | 9/1958 | Schwope |
| 3,149,941 | A | | 9/1964 | Barnitz et al. |
| 4,266,277 | A | | 5/1981 | Issenmann |
| 4,298,572 | A | | 11/1981 | Moffet et al. |
| 4,397,742 | A | | 8/1983 | Minnick |
| 4,492,862 | A | | 1/1985 | Grynberg et al. |
| 4,635,735 | A | | 1/1987 | Crownover |
| 4,887,464 | A | | 12/1989 | Tannenbaum et al. |
| 4,894,170 | A | * | 1/1990 | Billmyre ...................... 210/712 |
| 5,868,805 | A | * | 2/1999 | Nilsson ...................... 48/198.3 |
| 6,082,549 | A | * | 7/2000 | Gommel et al. ............. 209/164 |
| 6,276,190 | B1 | | 8/2001 | Zamfes |
| 6,631,567 | B1 | * | 10/2003 | Have ............................... 34/476 |
| 6,946,017 | B2 | * | 9/2005 | Leppin et al. ................. 95/139 |
| 8,171,772 | B2 | * | 5/2012 | Richards ..................... 73/23.41 |
| 2001/0035043 | A1 | | 11/2001 | Richards |

* cited by examiner

*Primary Examiner* — Max Noori
(74) *Attorney, Agent, or Firm* — Kermit D. Lopez; Luis M. Ortiz; Oritz & Lopez, PLLC

(57) ABSTRACT

An improved gas analyzer for analyzing the concentrations and amounts of one or more different gases in drilling mud returning from a borehole is disclosed. An oil well drilling rig re-circulates the drilling mud by continuously pumping it through a gas separation means. The gas separation means generally includes a fluid stop, a bubble jar and a dririte chamber in order to separate the gases from the drilling mud. A gas sample from these separated gases can be mixed with a carrier gas and are conveyed to gas analyzing means where the concentration of the different hydrocarbon components of the gases in the mud can be continuously measured.

7 Claims, 3 Drawing Sheets

GAS ANALYZER

CROSS REFERENCE TO RELATED APPLICATIONS

This patent application is a continuation of U.S. patent application Ser. No. 12/514,951 entitled "Gas Analyzer," which was filed on May 14, 2009 now U.S. Pat. No. 8,171,772, and which is the U.S. national phase application of International Application No. PCT/US08/79722, filed on Oct. 13, 2008 under the PCT (Patent Cooperation Treaty), which designated the US and claims priority to U.S. Provisional Patent Application No. 60/981,873, filed Oct. 23, 2007. The entire contents of these applications are incorporated herein by reference.

TECHNICAL FIELD

Embodiments are generally related to drilling and/or environmental operations. Embodiments are additionally related to well logging techniques utilized during drilling operations. Embodiments are also related to methods and systems for analyzing the concentration and amount of gas produced from mud during drilling of an oil well.

BACKGROUND OF THE INVENTION

In oil well drilling operations, a drill bit can be mounted on the end of an elongated rotating drill string which turns the bit and causes it to cut away the underlying earth and rock formations. During this operation, a drilling mud is continuously pumped down through the drill string and into the region around the drill bit and then back up to the surface. This drilling mud is typically made up of clays, chemical additives and/or an oil or water base and performs two important functions. First, the drilling mud acts as a coolant and lubricates the drill bit during operation and it collects the drill cuttings and carries them back to the surface of the well. Second, the drilling mud also serves to maintain a hydrostatic pressure, which prevents pressurized gases from the earth from blowing out through the drilled well. In addition, the mud may pick up and entrain gases present in the bottom of the well and deliver them to the surface along with the drill cuttings.

Drilling mud generally constitutes a liquid carrier, typically water or diesel oil, which is mixed with additives. In the case of a water-based mud, this may include bentonite day and various chemicals. The mud carries out several functions for assisting in the drilling process, including carrying away cuttings and fine solids produced by the drill bit as it bores through the rock. Entrained solids raise the mud's density and viscosity, leading to many drilling problems, including a reduced rate of penetration, loss of mud downhole and filter cake buildup. The portion of the drilling mud being returned from the well which includes various gaseous components to be analyzed must be separated from the mud.

It has been common in the past to provide a log of the drilling operation that will permit the nature of the earth formation through which the drill bit is penetrating. The log enables the drilling operator to ascertain the presence of oil or gas in the formation being drilled and also the location of such oil or gas in the well. As part of this logging operation, samples of the drill cuttings from predetermined depths of the well are collected and analyzed. Generally, these samples can be collected to represent a desired interval of drilling, such as every ten feet of well drilled or every thirty feet drilled.

In a majority of prior art mud logging systems, the information recorded from the drilling mud reaching the surface of the well, is generally done on a manual basis. All of the measurements and the measuring equipment require constant supervision so a logging operation generally involves two mud loggers each working alternate twelve-hour shifts. The well mud logging techniques have also made use of gas chromatography to ascertain the presence of different hydrocarbon species in the mud being returned. The gas chromatography technique involves taking samples of gas from the drilling mud and passing that gas through special columns filled with materials that allow different gases to flow at different rates. A further disadvantage of the prior art chromatographic gas analysis technique results from the fact that it is not possible to separate all of the hydrocarbon gas from the returning mud and therefore it is not possible with chromatographic analysis to ascertain the actual concentration of any species in the mud.

Based on the foregoing it is believed that a need exists for an improved system and method for analyzing the concentrations and amounts of one or more different gases from the mud produced by drilling an oil well.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for improved well logging during drilling.

It is another aspect of the present invention to provide for improved system and method for analyzing the concentrations and amounts of one or more different gases in drilling mud returning from the borehole.

The aforementioned aspects and other objectives and advantages can now be achieved as described herein. An improved gas analyzer for analyzing the concentrations and amounts of one or more different gases in drilling mud returning from a borehole is disclosed. An oil well drilling rig re-circulates the drilling mud by continuously pumping it through a gas separation means. The gas separation means generally includes a fluid stop, a bubble jar and a dririte chamber in order to separate various gaseous components from the drilling mud. A gas sample from these separated gases can be mixed with a carrier gas and are conveyed to gas analyzing means where the concentration of the different hydrocarbon components of the gases in the mud are continuously measured.

The carrier air can be passed through a silica gel scrubber and to a pump (e.g., Thomas pump), thereby maintaining the flow of the carrier air within predetermined parameters. The sample gas from the dririte chamber along with the carrier air is subjected to analysis in gas analyzing means to produce a component gas signal whose value corresponds to the concentration of the component in the gas mixture. The carrier air is simultaneously flowed at a rate such that the volume of carrier air is at least several times greater than the volume of the sample gas in the drilling mud.

The sample gas is continuously subjected to different analysis in the gas analyzing means to produce different gaseous component concentration signals whose values at any instant represent, respectively, the concentrations at that instant of the different gaseous components in the separated gas. These different gaseous component concentration signals are processed continuously in signal processing means to provide a continuous logging signal and thus provides an indication of the instantaneous concentration of the different gaseous components in the drilling mud.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the de ailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
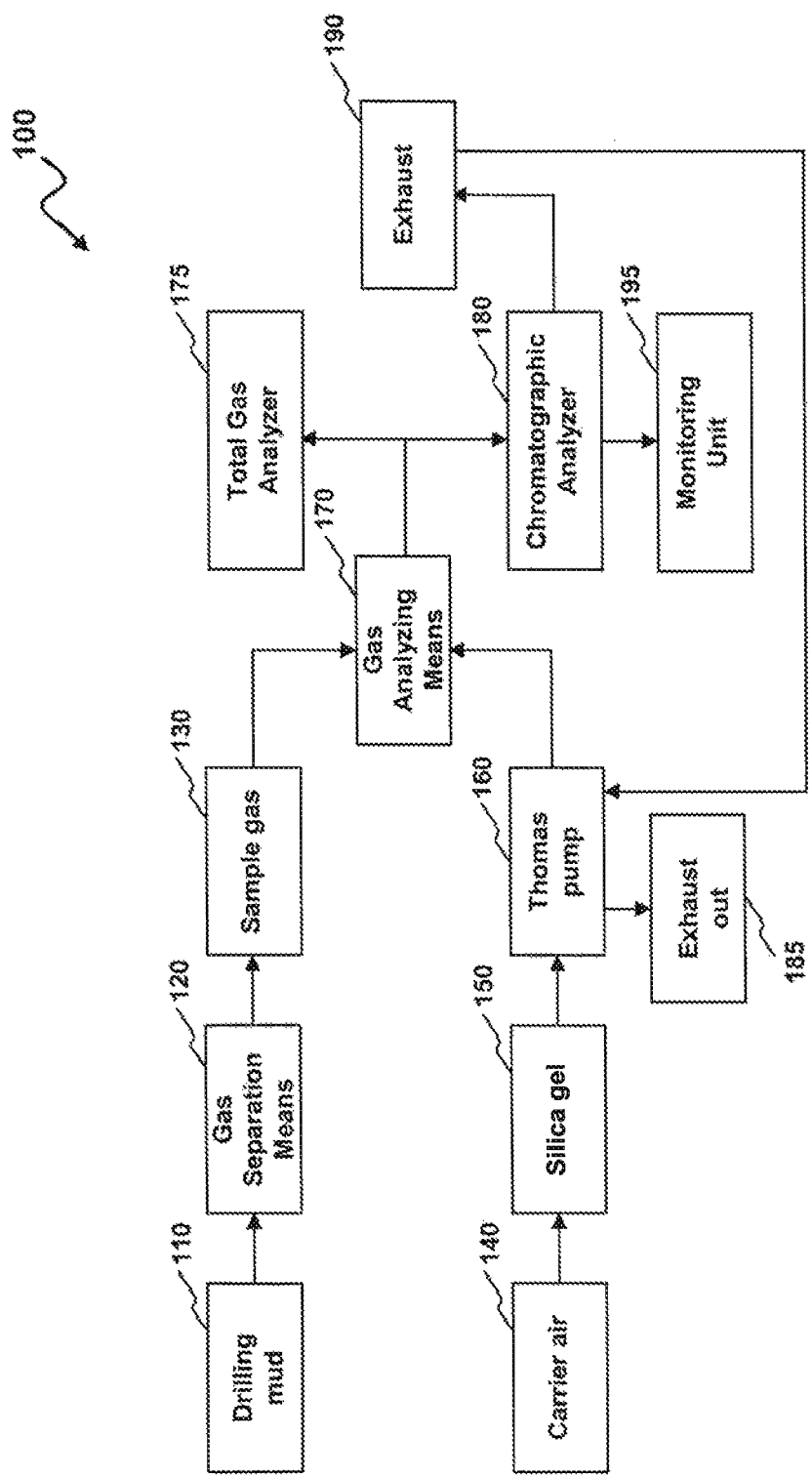
FIG. 1 illustrates a block diagram showing the major components of a mud analysis system, in accordance with a preferred embodiment.

Referring to FIG. 1 a block diagram showing the major components of a mud analysis system 100 is illustrated, in accordance with a preferred embodiment. The drilling mud analysis system 100 includes a gas separation means 120, a gas analyzing means 170 and a monitoring unit 195. The drilling mud 110 passes through the gas separation means 120 whereby the gas which includes various gaseous components to be analyzed can be separated from the drilling mud 110. The sample gas 130 extracted from the drilling mud 110 can be directed to the gas analyzing means 170 where the sample gas 130 can be analyzed to ascertain their constituent parts and where other measurements are made. A carrier air 140 from a silica gel scrubber 150 can be passed through a pump 160 (e.g., a Thomas pump) to the gas analyzing means 170. The Pump 160 can be adjusted in response to varying pressures and volumes of the carrier air 140 and thereby maintaining the flow of the carrier air 140 within predetermined parameters. The outlet of the pump 160 can be connected to the gas analyzing means 170 where various chemical and electrical tests are performed on the sample gas 130.

Atmospheric air is chosen as the carrier air 140 because of its ready availability and because it is relatively inert with respect to the hydrocarbons contained in the sample gas 130. Other gases, such as nitrogen, may be used, for example where the ambient air contains an excess of impurities which could affect the sample gas measurements. The sample gas 130 is evenly mixed with the carrier air 140 and the amount of each individual gas can be determined by a Chromatograph (CG) analyzer 180 and the results can be monitored utilizing the monitoring unit 195. For example, the quantity of methane, ethane, propane, isobutane, butane and pentane can each measured by the chromatograph analyzer 180. Similarly, the total gas from the sample gas 130 can be analyzed by the Total Gas Analyzer (TGA) 175 to determine the total amount of gases produced. The exhaust 190 from the gas analyzing means 170 is then transferred to the Pump 160 which controls the flow of the gas 130 and 140 and disposing the gas via an exhaust out 185.

Figure 2:
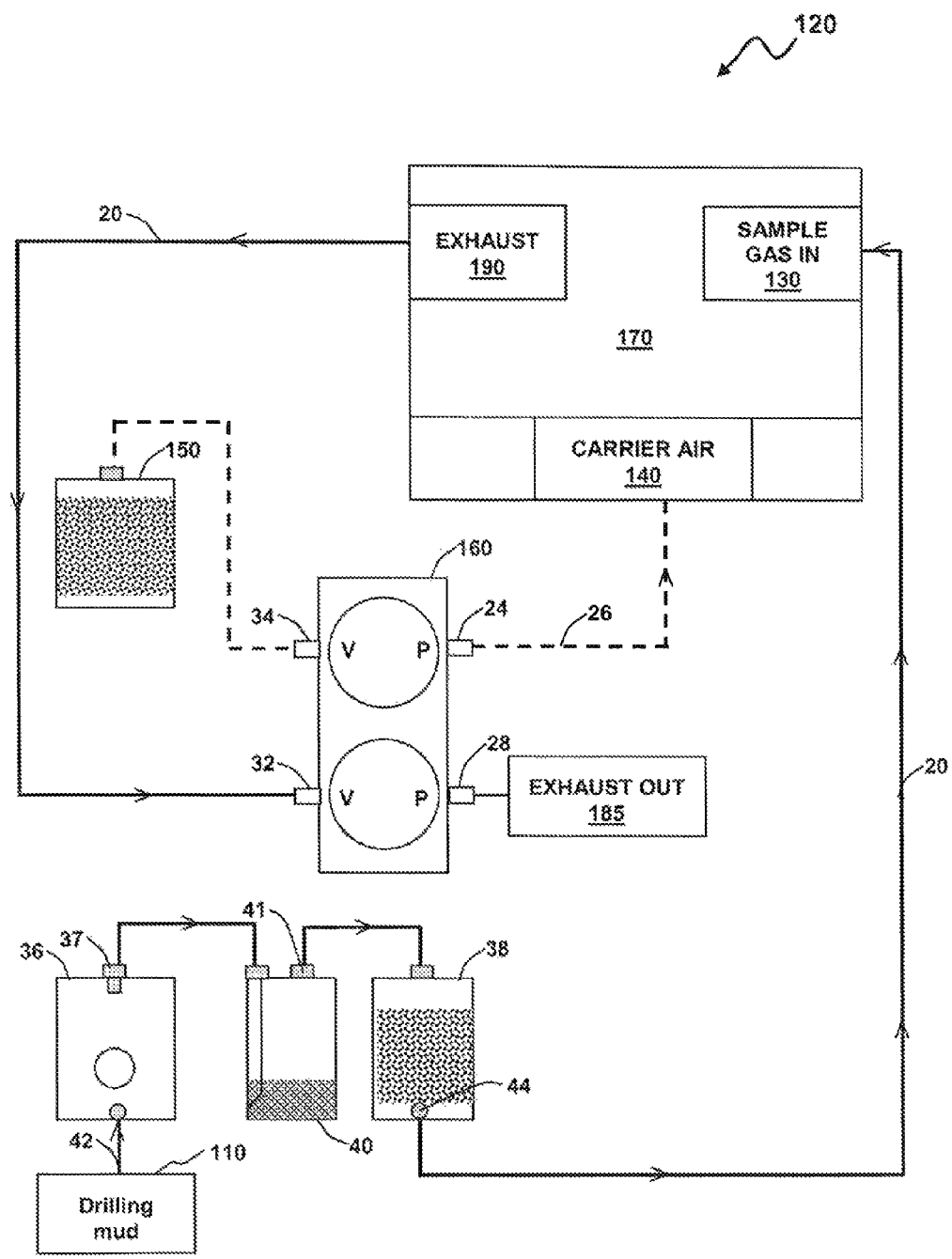
FIG. 2 illustrates a schematic representation of a gas separation means for separating gases from the drilling mud, in accordance with a preferred embodiment.

Referring to FIG. 2, a schematic representation of a gas separation means 120 for separating gases from the drilling mud 110 is illustrated, in accordance with a preferred embodiment. Note that in FIGS. 1-3, identical or similar parts or elements are generally indicated by identical reference numerals. The drilling mud 110 is generally captured from a drilling well (not shown). As stated before the process of capturing drilling mud 110 from the mud pit is well known in the art. The mud 110 passes through the gas separation means 120 where gases contained in the mud 110 can be extracted. The gas separation means 120 comprises an inlet line 42 connected to a fluid stop 36 wherein the mud sample gas 130 to be analyzed can be taken from the mud 110 just entering the gas separation means 120. The fluid stop 36 can be utilized as a check flow stop, which removes any solid matter, so that drilling mud 110 does not enter the gas analyzing means 170.

Since the rate of mud flow through the well and the depth of the well are known, it is possible to relate the mud sample analysis to the location in the earth to which it pertains. The outlet 37 of the fluid stop 36 is connected to a bubble jar 40. The bubble jar 40 can be filled with ethylene glycol in order to scrub it of water. A one-liter bubble jar 40 filled with 250 milliliters of ethylene can be installed between the fluid stop 36 and the outlet 41. The outlet 41 of the bubble jar 40 can be attached to "Dririte" chamber 38 with an outside exhaust 44. "Dririte" is ground anhydrite, which can be treated with an indicator that turns from blue to pink when saturated with water wherein some will be in its natural white state.

The carrier air 140 from the silica gel scrubber 150 can be passed through an inlet 34 of a pump 160. The outlet 24 of the Pump 160 is connected to the gas analyzing means 170 thereby maintaining the flow of the carrier air 140 within predetermined parameters. The flow of the sample gas 130 is indicated by line 20 and the flow of carrier air 140 is indicated by line 26. The carrier air 140 is simultaneously flowed through the gas analyzing means 170 at a rate such that the volume of carrier air 140 is at least several times greater than the volume of mud sample gas 130 in the drilling mud 110. The carrier air 140 can be taken from inside the unit in order to maintain a constant temperature.

Figure 3:
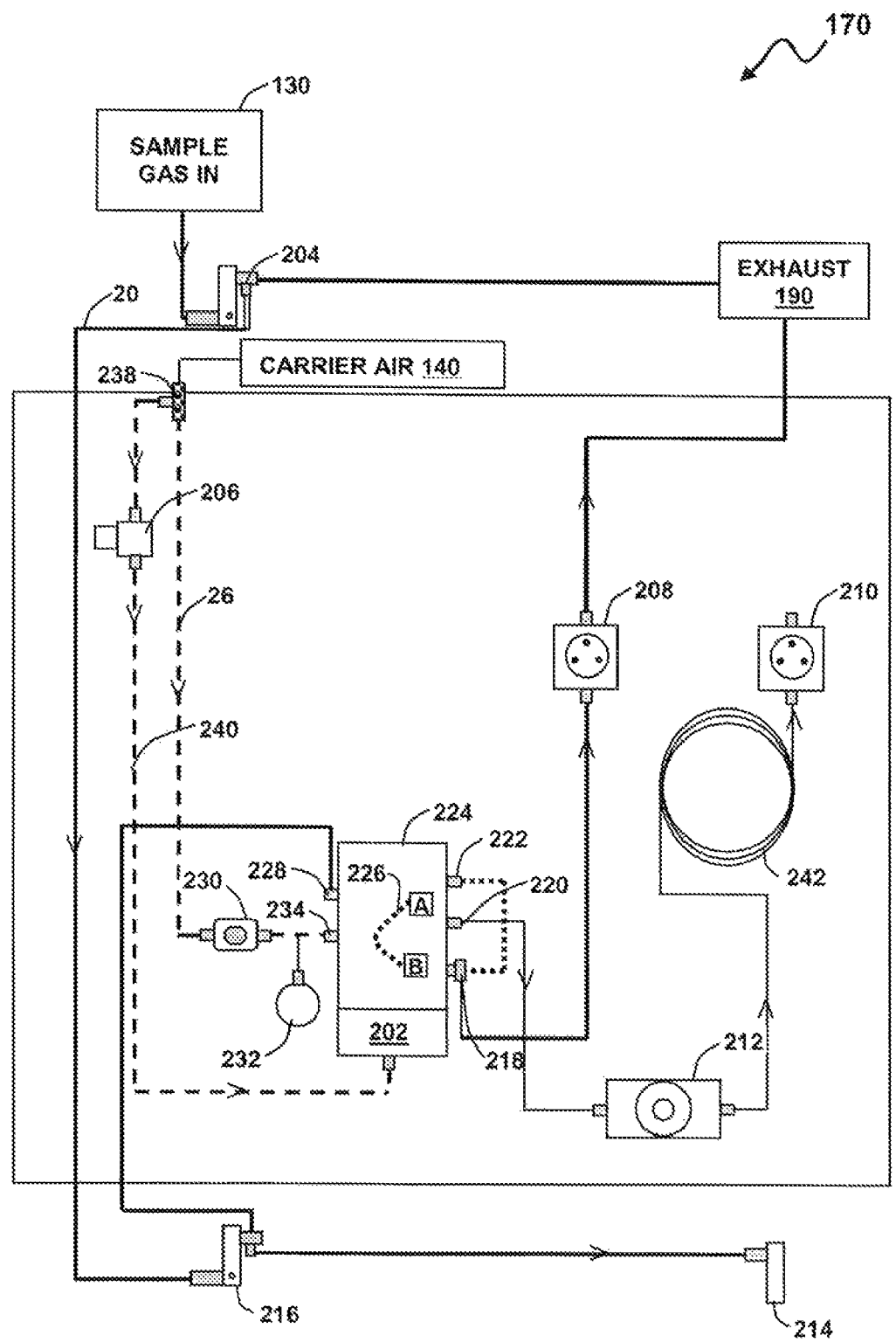
FIG. 3 illustrates a schematic representation of a gas analyzing means for analyzing the gaseous components in the gas separated from the drilling mud, in accordance with a preferred embodiment.

Referring to FIG. 3 a schematic representation of a gas analyzing means 170 for analyzing the gaseous components in the gas separated from the drilling mud 110 is illustrated, in accordance with a preferred embodiment. Note that in FIGS. 1-3, identical or similar parts or elements are generally indicated by identical reference numerals. The carrier air 140 flows through a flow control valve 238 wherein a portion of the carrier aft 140 passes through a solenoid valve 206, which controls the flow of the carrier air 140. The line 240 is connected to activator 202 of the sample valve 224. The activator 202 will move a diaphragm which will shift a plunger in the sample valve 224 which will change the connections of the ports. The majority of the carrier air 140 passes on through a pressure regulator 230. Pressure gauge 232 can be utilized to display the pressure.

The sample valve 224 includes seven ports identified as AIR IN PORT 234, GAS IN PORT 228, LOOP PORT A, LOOP PORT B, GAS IN PORT 218, CG PORT 220 and AIR IN PORT 222. The sample gas 130 can be captured at a rate anywhere from 3 standard cubic feet an hour (scfh) to 10 scfh. Normally it will be adjusted to capture about 6 scfh. Flow rotor 204 can be set to have an output of 6 scfh to flow control valve 216 which will exhaust 3 scfh. The output of the flow control valve 216 is connected to GAS IN PORT 228 and to valve 214. Thus, sample gas 130 from the mud pit circulates through the loop 226 as well as directly into the total gas analyzer 175 as shown as filament 208 in FIG. 3. The port 222 and 218 is coupled and the output is passed through the filament 208 and to the exhaust 190. The filament 208 actually comprises of two platinum filaments (not shown) with a common node, which acts as a total gas detector. One filament is sealed which acts as a reference filament. The other is open to the flow of sample gas 130 across it when fitted into the filament 208. The filament 208 can be configured in a Wheatstone bridge configuration.

Similarly, the output from CG port 220 is passed through a chromatograph 212. The solenoid valve 206 can be controlled by a timer (not shown) so that every 5 minutes it activates to open the solenoid valve 206 so that line 240 is connected to activator 202 of the sample valve 224. The activator 202 will move a diaphragm which will shift a plunger in the sample valve 224 which will change the connections of the ports. The preferred form of the sample valve 224 is a plunger running through a sleeve. O-rings on the plunger fit along the sleeve so that when the plunger is moved by the activator 202 that it will make the connections as described. It can be appreciated, however, that in accordance with other embodiments, other means can be utilized to make these connections. The plunger type operation is preferred because of its compact size.

The gas within the loop 226 can be expelled through LOOP PORT A which is connected to the CG PORT 220, when the valve 224 is switched from normal to closed position. The air 140 from AIR IN PORT 234 flows through LOOP PORT B. The air will push the accumulated gas in this path, the loop 226, out through the CG PORT 220 which can take the gas through the chromatograph reader 212, a separator 242 and filament 210. The separator column 242 is made of copper ¼ in. O.D. copper tubing 70 inches in length. It is coiled to conserve space. The column 242 is packed with granulated diabutial phthilate, a product manufactured by Kodak Chemical of Rochester N.Y. It is provided as a liquid rubber. The packing is placed into the copper tubing forming the separation column 242.

The chromatograph 212 can show the amounts of each of the gases present. Methane comes out of the CG PORT 220 and can be measured as a pulse across the filament bridge 210. It is followed by ethane, propane, isobutane, and normal butane in order of ascending molecular weight. As is well known, the chromatograph 212 will measure the first gas to be released from the column 242 which will be the methane. After the methane is measured, the second gas to be released from the separator may be ethane, after it is measured the next will be propane and so forth to pentane. The measurement of the amount of gases is the same in the total gas analyzer filament 208 and the chromatograph 212. The gases are measured by the heat units they produce as they are flowed over a heated special material.

Traditionally the material was platinum. In a preferred embodiment, the material for the filament can be a thermistor bead. The thermistor beads are a product of J. J. Enterprises in Baton Rough, La. It can be appreciated, however, that in accordance with other embodiments, other material can be utilized. Also in the event that there was some possibility there can be sufficient amounts of gases to cause the total gas analyzer 175 to go off the scale, (exceed its capacity) then it is possible to have an air dilution stream connected from an air flow to the flow control valve 238. An equal amount of aft is pumped into flow control valve 238. Therefore diluting the sample going to the total gas analyzer 175 to one half the otherwise calculated value. The exhaust 190 from the gas analyzing means 170 is then transferred to the pump 160 through the net 32 which controls the flow of the gas 130 and 140 and disposing the gas via an outlet 28 to the exhaust out 185.

Furthermore by providing appropriate additional valves, calibration gas sources and gas separation devices, it is possible to provide purging and calibration of the gas analyzing means 170 as well as backwashing of the gas separation means 120 so that different tests can be performed in rapid sequence.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for analyzing the concentrations and amounts of one or more different gases from a drilling rig, comprising:
    subjecting at least one portion of a drilling mud being returned from a well to a gas separation means to separate all of a gas containing a plurality of gaseous component from said at least one portion of said drilling mud;
    continuously subjecting a sample of said gas from said gas separation means and a carrier air from a pump to a gas analyzing means to produce said plurality of gaseous component concentration signal whose value at any instant corresponds to said sample gas; and
    thereafter redirecting said sample of said gas from said gas analyzing means to said pump which controls the flow of said gas and disposing said gas via an exhaust out, wherein said gas separation means comprises a fluid stop to remove a plurality of solid matter entering said gas analyzing means.

2. The method of claim 1 further comprising splitting a flow of said sample of said gas and said carrier air in a sample valve into a TGA (Total Gas Analyzer) column and a CG (Chromatograph) column.

3. The method of claim 1 further comprising adjusting said Pump in response to varying pressures and volumes of said carrier air from a silica gel scrubber and thereby maintaining the flow of said carrier air within predetermined parameters.

4. The method of claim 1 wherein said gas separation means comprises a bubble jar to remove water from said sample entering said gas analyzing means.

5. The method of claim 4 further comprising splitting a flow of said sample of said gas and said carrier air in a sample valve into a TGA (Total Gas Analyzer) column and a CG (Chromatograph) column.

6. The method of claim 1 wherein said gas separation means comprises a Dryrite chamber comprising a ground anhydrite such that water vapor does not come into contact said chromatograph column.

7. The method of claim 2 wherein said TGA column and said CG column comprise a filament in a Wheatstone bridge configuration.

* * * * *